(12) United States Patent
Ou Yang

(10) Patent No.: US 11,313,620 B2
(45) Date of Patent: Apr. 26, 2022

(54) INTELLIGENT DRYING METHOD AND ULTRAVIOLET STERILIZATION CONTAINER

(71) Applicant: SHENZHEN UVLED OPTICAL TECHNOLOGY CO., LTD., Shenzhen (CN)

(72) Inventor: Chenyi Ou Yang, Yongzhou (CN)

(73) Assignee: SHENZHEN UVLED OPTICAL TECHNOLOGY CO., LTD., Shenzhen (CN)

( * ) Notice: Subject to any disclaimer, the term of this patent is extended or adjusted under 35 U.S.C. 154(b) by 414 days.

(21) Appl. No.: 16/477,002

(22) PCT Filed: Apr. 29, 2019

(86) PCT No.: PCT/CN2019/085041
§ 371 (c)(1),
(2) Date: Jul. 10, 2019

(87) PCT Pub. No.: WO2020/206765
PCT Pub. Date: Oct. 15, 2020

(65) Prior Publication Data
US 2021/0348843 A1    Nov. 11, 2021

(30) Foreign Application Priority Data

Apr. 11, 2019 (CN) .......................... 201910289543.2

(51) Int. Cl.
*F26B 3/04* (2006.01)
*A61L 2/10* (2006.01)
(Continued)

(52) U.S. Cl.
CPC ...... *F26B 3/04* (2013.01); *A61L 2/10* (2013.01); *F26B 21/02* (2013.01); *F26B 21/06* (2013.01);
(Continued)

(58) Field of Classification Search
CPC .. F26B 3/04; F26B 21/02; F26B 21/06; A61L 2/10
(Continued)

(56) References Cited

U.S. PATENT DOCUMENTS 5,713,137 A * 2/1998 Fujita ..................... A61L 2/06
34/106
5,836,086 A * 11/1998 Elder ....................... F26B 3/04
34/396
(Continued)

*Primary Examiner* — Stephen M Gravini
(74) *Attorney, Agent, or Firm* — Li & Cai Intellectual Property (USA) Office

(57) ABSTRACT

An intelligent drying method and an ultraviolet sterilization container are applied to an ultraviolet sterilization container for drying a sterilized article, the method comprising: that the sterilization container sequentially executes the following steps after receiving a drying instruction: releasing hot air to an article storage cavity; when an initial drying time is reached, collecting the intracavity temperature of the article storage cavity; automatically obtaining an extended drying time corresponding to the intracavity temperature of the article storage cavity; and continuously releasing hot air to the article storage cavity until the extended drying time is reached. The ultraviolet sterilization container includes: an article storage cavity, a heating air duct, a microprocessor, and a memory storing a computer readable program executable by the microprocessor. When the computer readable program is executed by the microprocessor, the sterilization container performs the above steps.

8 Claims, 4 Drawing Sheets

(51) Int. Cl.
*F26B 21/02* (2006.01)
*F26B 21/06* (2006.01)
*F26B 23/06* (2006.01)
*F26B 25/06* (2006.01)
*F26B 25/16* (2006.01)

(52) U.S. Cl.
CPC ............ F26B 23/06 (2013.01); F26B 25/063 (2013.01); F26B 25/16 (2013.01); *A61L 2202/122* (2013.01); *A61L 2202/16* (2013.01)

(58) Field of Classification Search
USPC ............................................................. 34/60
See application file for complete search history.

(56) References Cited

U.S. PATENT DOCUMENTS

| | | | | |
|---|---|---|---|---|
| 6,971,187 B1 * | 12/2005 | Pikal | ......................... | F26B 5/06 |
| | | | | 34/285 |
| 7,171,761 B1 * | 2/2007 | Hunts | .................... | D06F 58/10 |
| | | | | 34/91 |
| 8,850,715 B2 * | 10/2014 | Swoboda | ................. | F26B 21/14 |
| | | | | 34/381 |
| 9,644,891 B2 * | 5/2017 | Zielinski | .................... | F26B 3/02 |
| 11,066,778 B2 * | 7/2021 | D'Anna | .................. | F26B 3/347 |
| D928,429 S * | 8/2021 | Ou Yang | .......................... | D32/1 |

* cited by examiner

INTELLIGENT DRYING METHOD AND ULTRAVIOLET STERILIZATION CONTAINER

BACKGROUND

1. Technical Field

The invention relates to the field of disinfection technology, in particular to an intelligent drying method applied to an ultraviolet sterilization container for drying a sterilized article, and an ultraviolet sterilization container adopting the intelligent drying method.

2. Description of Related Art

Ultraviolet light has a good bactericidal effect and is widely used in the field of disinfection. UV sterilization containers are one of the main applications of UV light in the field of sterilization. The sterilization method of the ultraviolet sterilization container is to use the illumination device to radiate ultraviolet light to the article storage cavity, and the ultraviolet light directly irradiates the sterilized article to kill the bacteria on the surface of the sterilized article to achieve the purpose of sterilization.

Because water stains often remain on the sterilized article, in order to automatically remove residual water stains, the portable UV sterilization container will be provided with a heating air duct, and the hot air duct can automatically release hot air to the storage space to dry the sterilized article. The existing drying method is to control a fixed operation time of the heating air duct. However, the drying method has the following drawbacks. 1. Drying is unreliable and energy is wasted. Due to factors such as the ambient temperature and the amount of the sterilized article, sometimes the sterilized article is not completely dried, and sometimes the drying is continued after the sterilized article is dried, that is, there is the phenomenon of "under-drying" and "over-drying", in which when "over-drying", energy is wasted. 2. If a variety of sensors are installed to monitor various factors affecting drying, the cost will be greatly increased.

SUMMARY

The object of the present invention is to provide an intelligent drying method and an ultraviolet sterilization container to solve the problem of "under-drying" and "over-drying" in the fixed drying time without additional cost.

In order to achieve the above object, the technical solution adopted by the present invention is as follows.

An intelligent drying method is applied to an ultraviolet sterilization container for drying a sterilized article, wherein the intelligent drying method comprises that the sterilization container sequentially executes the following steps after receiving a drying instruction: releasing hot air to an article storage cavity; when an initial drying time is reached, collecting the intracavity temperature of the article storage cavity; automatically obtaining an extended drying time corresponding to the intracavity temperature of the article storage cavity; and continuously releasing hot air to the article storage cavity until the extended drying time is reached.

Preferably, in the step of releasing hot air to the article storage cavity, an inner circulation mode is adopted, and the inner circulation mode circulate the air such that air of the article storage cavity entering an air duct of the cavity wall of the article storage cavity from an return air outlet, being heated in the air duct, and then delivered to the article storage cavity from an air outlet.

Preferably, the initial drying time is any value between 30 minutes and 90 minutes.

Preferably, in the step of automatically obtaining an extended drying time corresponding to the intracavity temperature of the article storage cavity, the extended drying time comprises four types, and the correspondence between each drying time and intracavity temperature is as follows, wherein: when the intracavity temperature is lower than 33 degrees Celsius, the drying time is extended by 90 minutes; when the intracavity temperature is between 33-40 degrees Celsius, the drying time is extended by 60 minutes; when the intracavity temperature is between 40-44 degrees Celsius, the drying time is extended by 30 minutes; and when the intracavity temperature is higher than 44 degrees Celsius, the drying time is extended by 0 minute.

An ultraviolet sterilization container, comprises: an article storage cavity for accommodating a sterilized article; a heating air duct for releasing hot air to the article storage cavity; a microprocessor electrically coupled to the heating air duct; and a memory storing a computer readable program executable by the microprocessor; and wherein the sterilization container performs the steps of the intelligent drying method as mentioned above when the computer readable program is executed by the microprocessor.

Preferably, the heating air duct is an inner circulation type heating air duct, and the inner circulation type heating air duct comprises: the article storage cavity; an air outlet disposed in the cavity wall of the article storage cavity and communicating with the article storage cavity; a return air outlet that is open to the cavity wall of the article storage cavity and communicates with the article storage cavity; an air duct disposed in the interior of the cavity wall of the article storage cavity and communicating with the air outlet and the return air outlet; and a fan and an electric heating element mounted in the air duct; wherein an inner circulation type heating air duct is formed from the article storage cavity sequentially through the return air outlet, the air duct, the fan and the electric heating element, the air outlet, and the article storage cavity.

Preferably, the air outlet and the return air outlet are respectively opened in adjacent cavity walls of the article storage cavity.

Preferably, the inner circulation type heating air duct has two return air outlets, and the two return air outlet are respectively disposed on two opposite cavity walls of the article storage cavity.

Preferably, the air outlet and the return air outlet are a plurality of small holes distributed in an array.

Preferably, the electric heating element comprises a resistance wire and a frame having a sheet shape and a hollow portion; wherein the resistance wire is wound around the frame and a mesh structure is formed in the hollow portion.

Compared with the prior art, the present invention has at least the following beneficial effects.

With two-step drying, the drying time is adaptively determined by software, and the sterilized article can be dried accurately without wasting energy. Moreover, there is no need to add additional sensors and associated circuitry, so there is no additional cost.

Figure 1:
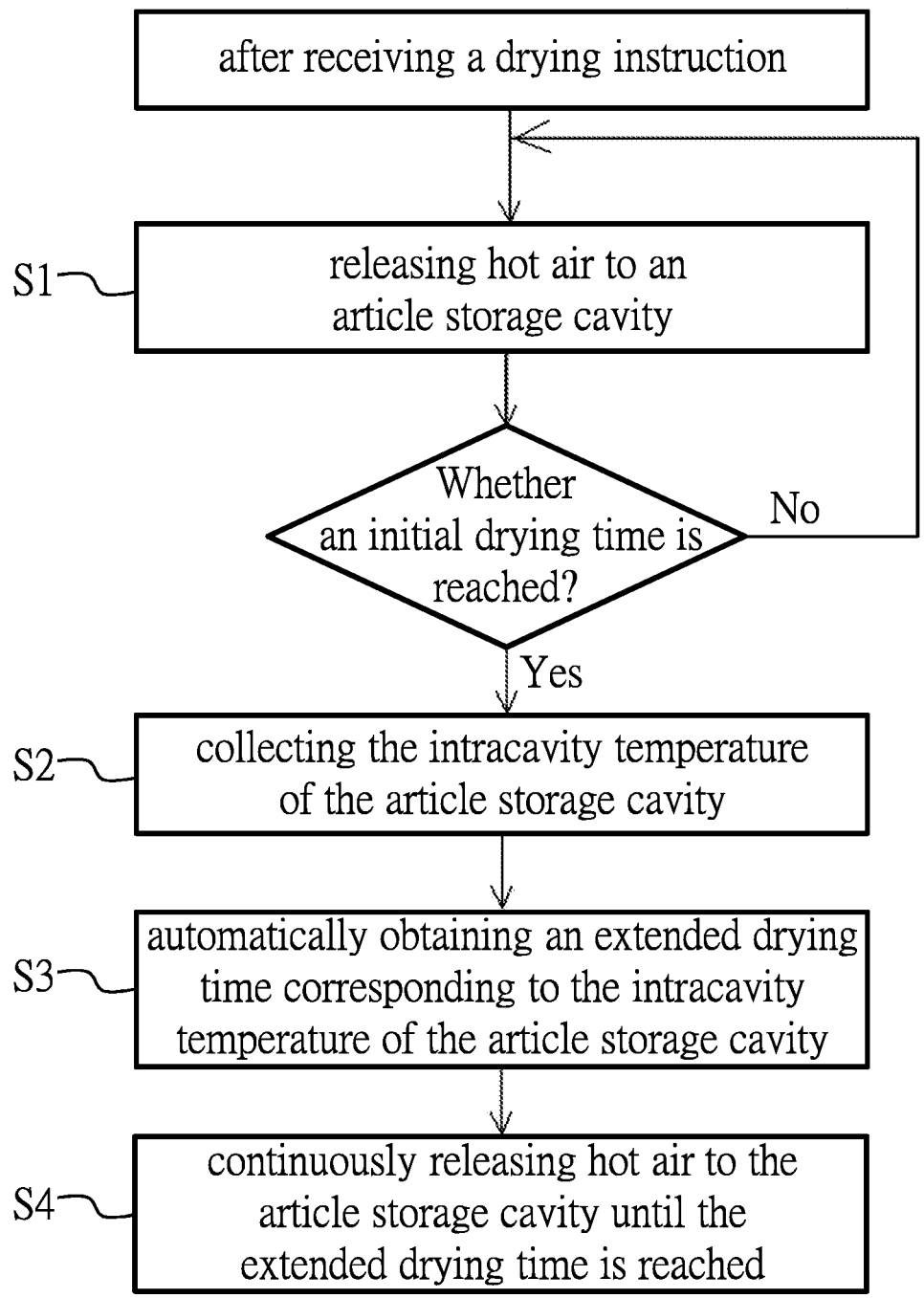
FIG. 1 is a flow chart of the intelligent drying method.

Reference numerals: 1, article storage cavity; 2, return air outlet; 3, air outlet; 4, sterilization container body; 5, handle; 6, illumination device (UV LED); 7, air duct; 7', fan; 8, electric heating elements; 9, frame; 10, resistance wire; 11, hollow portion.

DESCRIPTION OF THE EXEMPLARY EMBODIMENTS

The invention will be further described below in conjunction with the drawings and embodiments.

The intelligent drying method is applied to an ultraviolet sterilization container for drying a sterilized article.

Referring to FIG. 1, the intelligent drying method includes the following steps.

In step S1, hot air is released to the article storage cavity.

In step S2, when an initial drying time is reached, the intracavity temperature of the article storage cavity is collected. The initial drying time is a preset time value, and the initial drying time is preferably, but not limited to, any value between 30 minutes and 90 minutes.

In step S3, an extended drying time corresponding to the intracavity temperature of the article storage cavity is automatically obtained.

In an exemplary embodiment, the initial drying time is set to 60 minutes, and the extended drying time is divided into four types according to the intracavity temperature when the initial drying time is reached. When the intracavity temperature is lower than 33 degrees Celsius, the drying time is extended by 90 minutes; when the intracavity temperature is between 33-40 degrees Celsius, the drying time is extended by 60 minutes; when the intracavity temperature is between 40-44 degrees Celsius, the drying time is extended by 30 minutes; and when the intracavity temperature is higher than 44 degrees Celsius, the drying time is extended by 0 minute.

It should be noted that the above-mentioned types, specific temperature values and time values are only a typical embodiment, and these values can be flexibly set as needed. These values require prior experiments to ensure that the sterilized article is just dried when these values are applied. The more the types are, the better the control accuracy is, but it will increase the complexity of the operation.

In step S4, the hot air is continuously released to the article storage cavity until the extended drying time is reached.

It can be seen that the above intelligent drying method adopts two-step drying, and the drying time is adaptively determined by software, and the sterilized article can be accurately dried without wasting energy. Moreover, there is no need to add additional sensors and associated circuitry, so there is no additional cost.

Further, in the step of releasing hot air to the article storage cavity, an inner circulation mode is adopted, and the inner circulation mode includes: air of the article storage cavity entering the air duct of the cavity wall of the article storage cavity from the return air outlet, being heated in the air duct, and then delivered to the article storage cavity from an air outlet. In this way, the circulating air is hot air, and the air can be heated to the required temperature with a small amount of energy, thereby further saving energy.

Further, the initial drying time is any value between 30 minutes and 90 minutes. During this time, there will be no phenomenon of "over-drying", and a sufficiently long initial time will help to predict the drying process more accurately.

Further, in the step of automatically obtaining an extended drying time corresponding to the intracavity temperature of the article storage cavity, the extended drying time comprises four types, and the correspondence between each drying time and intracavity temperature is as follows: when the intracavity temperature is lower than 33 degrees Celsius, the drying time is extended by 90 minutes; when the intracavity temperature is between 33-40 degrees Celsius, the drying time is extended by 60 minutes; when the intracavity temperature is between 40-44 degrees Celsius, the drying time is extended by 30 minutes; and when the intracavity temperature is higher than 44 degrees Celsius, the drying time is extended by 0 minute. Using the aforementioned four types can achieve better control accuracy, and the calculation is relatively simple.

Figure 2:
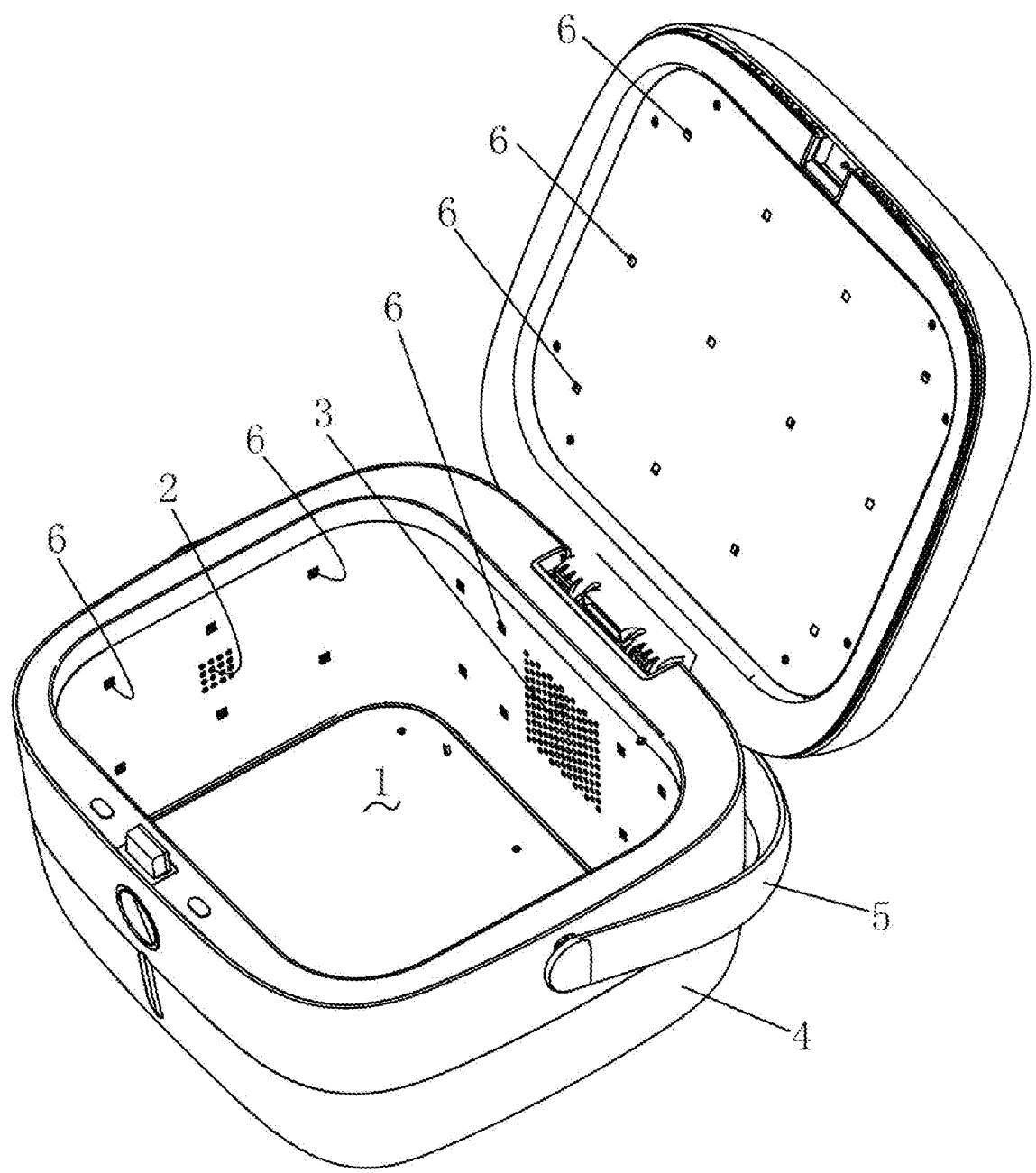
FIG. 2 is a schematic structural view of the article storage cavity, the illumination device, and the heating air duct of the sterilization container.
Figure 3:
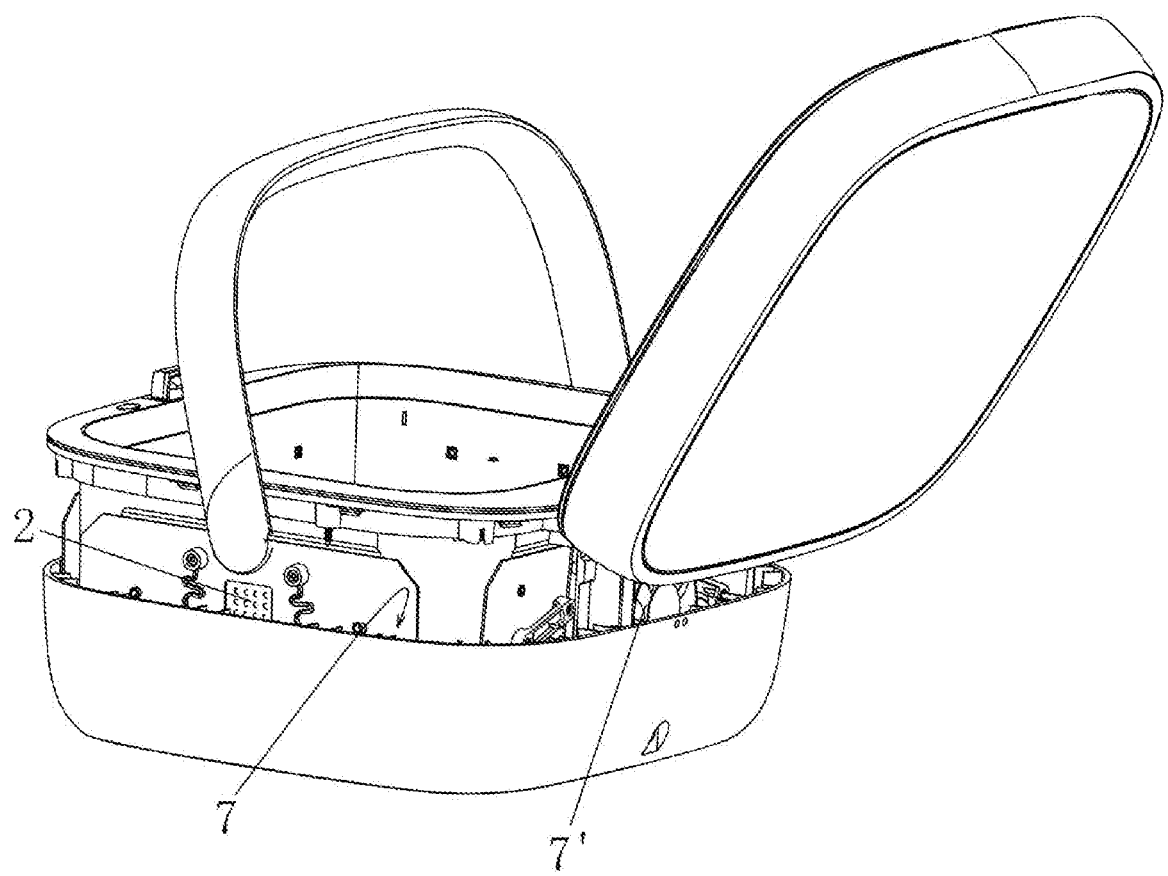
FIG. 3 is a schematic view of the fan and the air duct in the heating air duct.

Referring to FIG. 2 and FIG. 3, the ultraviolet sterilization container includes: an article storage cavity 1 for accommodating an article to be sterilized, an illumination device 6 disposed on a cavity wall of the article storage cavity 1 for releasing ultraviolet light (sterilization medium) to the article storage cavity 1, and a heating air duct disposed on a cavity wall of the article storage cavity 1 for releasing hot air to the article storage cavity 1.

Figure 4:
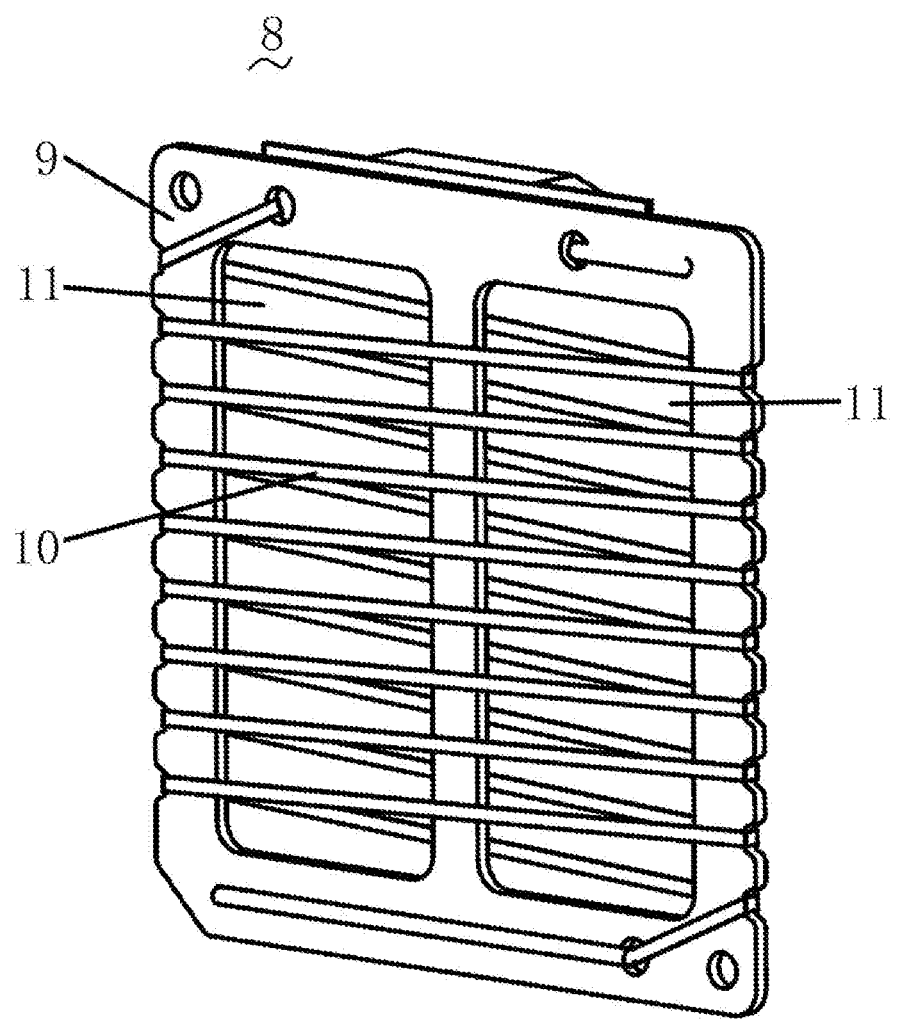
FIG. 4 is a schematic structural view of the electric heating element.

The heating air duct is an inner circulation type heating air duct, and the inner circulation type heating air duct includes: the article storage cavity 1; an air outlet 3 disposed on the cavity wall of the article storage cavity 1 and communicating with the article storage cavity 1; a return air outlet 2 disposed on the cavity wall of the article storage cavity 1 and communicating with the article storage cavity 1; an air duct 7 disposed in the interior of the cavity wall of the article storage cavity 1 and communicating with the air outlet 3 and the return air outlet 2; and a fan 7' and an electric heating element 8 installed in the air duct 7 (as shown in FIG. 4). The inner circulation type heating air duct is formed in sequence from the article storage cavity 1, the air return outlet 2, the air duct 7, the fan 7', the electric heating element 8, the air outlet 3, and the article storage cavity 1. In this way, when drying, no air is introduced from the environment, and the circulating air is hot air and the air can be heated to a required temperature by using less energy, which can save energy consumed by drying.

The ultraviolet sterilization container further includes a microprocessor (not shown) electrically coupled to the heating air duct, and a memory storing a computer readable program executable by the microprocessor; wherein the computer is readable, and the sterilization container performs the steps of the intelligent drying method described above when the program is executed by the microprocessor. The memory may be an on-chip memory of the microprocessor or an off-chip memory.

Further, the air outlet 3 and the return air outlet 2 are respectively disposed on the adjacent cavity wall of the article storage cavity 1. When the fan 7' is in operation, a negative pressure is generated at the return air outlet 2, and this negative pressure applies to the air in the article storage cavity 1, which promotes the diffusion of air. Compared with the air outlet 3 and the return air outlet 2 being disposed on the same side and the opposite sides, the positional design adopted in this embodiment can better diffuse the air entering the article storage cavity 1 from the air outlet 3.

Further, the inner circulation type heating air duct has two return air outlets 2, and the two return air outlets 2 are respectively disposed on opposite cavity walls of the article storage cavity 1. Compared with the return air outlet disposed only on one side, the design of the return air outlet on each of the opposite side walls makes the air diffusion effect in the article storage cavity 1 better.

Further, the air outlet 3 and the return air outlet 2 are a plurality of small holes distributed in an array. Compared with a large hole, a plurality of small holes distributed in the array can disperse the passing air, and can prevent articles from passing through the air outlet 3 and the return air outlet 2.

Further, as shown in FIG. 4, the electric heating element 8 comprises a resistance wire 10 and a frame 9 having a sheet shape and a hollow portion 11; wherein the resistance wire 10 is wound around the frame 9 and a mesh structure is formed in the hollow portion 11. With such an electric heating element 8, it can be easily fixed to the end of the fan 7', and the electric heating element 8 can be mounted very conveniently. Moreover, air can pass through the mesh structure, which can effectively increase the contact area of the air and the electric heating element, and achieve rapid and efficient heating of the flowing air.

The sterilization container is a portable UV sterilization container that can be used not only at home but also for use in the office or when going out. The sterilization container body 4 is provided with a handle 5.

The present invention has been described in detail with reference to the preferred embodiments thereof, and the detailed description is not to be construed as limiting the scope of the invention. Various refinements, equivalent transformations, and the like performed by the above-described embodiments under the present invention should be included in the scope of the present invention.

What is claimed is:

1. An intelligent drying method applied to an ultraviolet sterilization container, comprising the following steps which are executed by the ultraviolet sterilization container sequentially after receiving a drying instruction:
   releasing hot air to an article storage cavity that has a cavity wall;
   when an initial drying time is reached, collecting an intracavity temperature of the article storage cavity;
   automatically obtaining an extended drying time corresponding to the intracavity temperature of the article storage cavity; and
   continuously releasing hot air to the article storage cavity until the extended drying time is reached;
   wherein in the step of releasing hot air to the article storage cavity that has a cavity wall, an inner circulation mode is adopted, and the inner circulation mode includes: air of the article storage cavity entering an air duct of the cavity wall of the article storage cavity from an return air outlet, being heated in the air duct, and then delivered to the article storage cavity from an air outlet.

2. The intelligent drying method according to claim 1, wherein the initial drying time is any value between 30 minutes and 90 minutes.

3. The intelligent drying method according to claim 2, wherein in the step of automatically obtaining an extended drying time corresponding to the intracavity temperature of the article storage cavity, the extended drying time comprises four types, wherein:
   if the intracavity temperature is lower than 33 degrees Celsius, the drying time is extended by 90 minutes;
   if the intracavity temperature is between 33-40 degrees Celsius, the drying time is extended by 60 minutes;
   if the intracavity temperature is between 40-44 degrees Celsius, the drying time is extended by 30 minutes; and
   if the intracavity temperature is higher than 44 degrees Celsius, the drying time is extended by 0 minute.

4. An ultraviolet sterilization container, comprising:
   an article storage cavity configured to accommodate a sterilized article;
   a heating air duct configured to release hot air to the article storage cavity;
   a microprocessor electrically coupled to the heating air duct; and
   a memory storing a computer readable program executable by the microprocessor; and
   wherein the heating air duct is an inner circulation type heating air duct, and the inner circulation type heating air duct includes:
   an article storage cavity that has a cavity wall;
   an air outlet disposed in the cavity wall of the article storage cavity and communicating with the article storage cavity;
   a return air outlet that is open to the cavity wall of the article storage cavity and communicates with the article storage cavity;
   an air duct disposed in an interior of the cavity wall of the article storage cavity and communicating with the air outlet and the return air outlet;
   a fan mounted in the air duct; and
   an electric heating element mounted in the air duct;
   wherein the inner circulation type heating air duct is formed from the article storage cavity sequentially through the return air outlet, the air duct, the fan, the electric heating element, the air outlet, and the article storage cavity.

5. The ultraviolet sterilization container according to claim 4, wherein the air outlet and the return air outlet are respectively disposed in adjacent cavity walls of the article storage cavity.

6. The ultraviolet sterilization container according to claim 5, wherein the inner circulation type heating air duct has two return air outlets, and the two return air outlets are respectively disposed on two opposite cavity walls of the article storage cavity.

7. The ultraviolet sterilization container according to claim 4, wherein the air outlet and the return air outlet are a plurality of bores distributed in an array.

8. The ultraviolet sterilization container according to claim 4, wherein the electric heating element comprises a resistance wire and a frame having a sheet shape and a hollow portion; and wherein the resistance wire is wound around the frame and a mesh structure is formed in the hollow portion.

* * * * *